US010660977B2

(12) United States Patent
Iwasaki et al.

(10) Patent No.: US 10,660,977 B2
(45) Date of Patent: May 26, 2020

(54) METHOD FOR TREATING BIOLOGICAL TISSUE AND BIOLOGICAL TISSUE

(71) Applicant: WASEDA UNIVERSITY, Tokyo (JP)

(72) Inventors: Kiyotaka Iwasaki, Tokyo (JP); Mitsuo Umezu, Tokyo (JP)

(73) Assignee: WASEDA UNIVERSITY, Tokyo (JP)

( * ) Notice: Subject to any disclaimer, the term of this patent is extended or adjusted under 35 U.S.C. 154(b) by 0 days.

(21) Appl. No.: 14/389,269

(22) PCT Filed: Apr. 1, 2013

(86) PCT No.: PCT/JP2013/059842
§ 371 (c)(1),
(2) Date: Sep. 29, 2014

(87) PCT Pub. No.: WO2013/147299
PCT Pub. Date: Oct. 3, 2013

(65) Prior Publication Data
US 2015/0064228 A1    Mar. 5, 2015

(30) Foreign Application Priority Data

Mar. 31, 2012 (JP) ................................ 2012-083367

(51) Int. Cl.
*A61L 2/00* (2006.01)
*A61L 27/36* (2006.01)
*A01N 1/02* (2006.01)

(52) U.S. Cl.
CPC .......... *A61L 2/0094* (2013.01); *A01N 1/0221* (2013.01); *A01N 1/0226* (2013.01); *A61L 27/3687* (2013.01); *A61L 2430/40* (2013.01)

(58) Field of Classification Search
None
See application file for complete search history.

(56) References Cited

U.S. PATENT DOCUMENTS

| | | | |
|---|---|---|---|
| 5,334,841 A * | 8/1994 | Graessle | A61L 2/28 250/458.1 |
| 5,336,616 A | 8/1994 | Livesey et al. | |
| 6,632,648 B1 | 10/2003 | Kampinga et al. | |
| 2002/0128724 A1* | 9/2002 | Ollerenshaw et al. | 623/23.71 |
| 2004/0033160 A1* | 2/2004 | MacPhee | A61L 2/0029 422/22 |
| 2005/0186185 A1 | 8/2005 | Conrad et al. | |
| 2007/0249033 A1 | 10/2007 | Kampinga et al. | |
| 2008/0102439 A1* | 5/2008 | Tian | A61L 27/3604 435/1.1 |
| 2009/0164005 A1 | 6/2009 | Dove et al. | |
| 2009/0175954 A1 | 7/2009 | Kinoshita et al. | |
| 2010/0291532 A1* | 11/2010 | Ngo et al. | 435/1.1 |

FOREIGN PATENT DOCUMENTS

| | | |
|---|---|---|
| CN | 1550238 A | 12/2004 |
| CN | 101366976 A | 9/2009 |
| EP | 0564786 A2 | 10/1993 |
| JP | 06-261933 A | 9/1994 |
| JP | 2000-511519 A | 9/2000 |
| JP | 2006-526413 A | 11/2006 |
| JP | 2008-228744 A | 10/2008 |
| JP | 2011-005043 A | 1/2011 |
| WO | 1999058082 A2 | 11/1999 |
| WO | 2007/013331 A1 | 2/2007 |
| WO | 2010016942 A1 | 2/2010 |
| WO | 2011/019361 A1 | 2/2011 |
| WO | 2011/142407 A1 | 11/2011 |

OTHER PUBLICATIONS

Nakamura T et al., "The use of trehalose-treated freeze-dried amniotic membrane for ocular surface reconstruction", Biomaterials, 2008. vol. 27. pp. 3729-3737.
K.C. McGilvray et al., "Effects of 60Co gamma radiation dose on initial structural biomechanical properties of ovine bone—patellar tendon—bone allografts", Cell Tissue Bank, May 2011, pp. 89-98, vol. 12, Issue 2.
International Search Report dated May 21, 2013, issued in corresponding application No. PCT/JP2013/059842.

* cited by examiner

*Primary Examiner* — David J Blanchard
*Assistant Examiner* — Sarah J Chickos
(74) *Attorney, Agent, or Firm* — Westerman, Hattori, Daniels & Adrian, LLP

(57) ABSTRACT

The present invention suppresses the strength reduction or degeneration of a tissue after the tissue is dried and/or sterilized, for the tissue comprising biological components and the like. Specifically, biological tissue is immersed in a trehalose solution and shaken, thereby impregnating the biological tissue with the trehalose solution. The trehalose solution used here is one obtained by dissolving trehalose in a phosphate buffered saline, the concentration of trehalose being preferably in the range of 20 wt % to 35 wt %. Thereafter, the biological tissue is dried to remove moisture in the biological tissue, and sterilized with ethylene oxide gas.

10 Claims, No Drawings

METHOD FOR TREATING BIOLOGICAL TISSUE AND BIOLOGICAL TISSUE

TECHNICAL FIELD

The present invention relates to a method for treating biological tissue and to the biological tissue, and more specifically to a method for treating biological tissue so as to suppress the degeneration and strength reduction of the tissue due to sterilization, and a biological tissue obtained by the treatment method.

BACKGROUND ART

The present applicants have already proposed a method for acellularizing an animal tissue, such as pericardium or tendon, harvested from an animal, such as a cow or a pig, in order to transplant the animal tissue into a human body (see Patent Literature 1 and the like). Here, the biological tissue harvested from an animal and acellularized (hereinafter referred to as "acellularized tissue") may not be used immediately after the acellularization but sterilized for storage for the time being. In order to put such an animal-derived acellularized tissue to practical use, treatment for sterilizing the acellularized tissue is essential.

CITATION LIST

Patent Literature

Patent Literature 1: International Publication No. WO 2011/142407

SUMMARY OF INVENTION

Technical Problem

However, the application of sterilization to a tissue consisting of biological components (hereinafter referred to as "biological tissue") and the like leads to the significant damage of the biological tissue and reduces the strength of the tissue compared to that before the treatment. As a result of intensive experimental works, the present inventors have found that the lyophilization and sterilization of biological tissue followed by rehydration causes tissue degeneration in which the tissue has a lower moisture content and becomes harder than the biological tissue before the treatment. Accordingly, the present inventors have impregnated biological tissue with a trehalose solution before the sterilization of the biological tissue. As a result, it has been found that the impregnation can suppress strength reduction and tissue degeneration in the sterilized biological tissue.

The present invention has been worked out based on these findings, and an object thereof is to provide a method for treating biological tissue which can suppress strength reduction and tissue degeneration in the sterilized tissue comprising biological components and the like, and a biological tissue obtained by the treatment method.

Solution to Problem

In the present invention, a tissue consisting of biological components and the like (hereinafter referred to as "biological tissue") is immersed in a trehalose solution and shaken for about 24 hours to impregnate the biological tissue with the trehalose solution. The trehalose solution used here is one obtained by dissolving trehalose in a phosphate buffered saline, the concentration of trehalose being preferably in the range of 20 wt % to 35 wt %.

Thereafter, the biological tissue is dried to remove moisture in the biological tissue. The drying here is not particularly limited; however, it is carried out at a temperature of about −45° C. for about 24 hours.

Then, the tissue is sterilized with ethylene oxide gas. The conditions of the sterilization here are not particularly limited, and are set to a temperature of about 30° C. for suppressing collagen degeneration, an exposure time of about 12 hours, and an aeration of about 20 hours. It is also possible to adopt other sterilization methods, such as hydrogen peroxide low-temperature plasma sterilization. In the present invention, another oligosaccharide of disaccharide, such as sucrose, lactose, or maltose can be used in place of trehalose. In other words, various embodiments can be adopted as long as drying and sterilization are carried out after impregnating biological tissue with an oligosaccharide solution of a disaccharide as described above.

Advantageous Effect of Invention

According to the present invention, tissue degeneration and strength reduction can be suppressed in sterilized biological tissues.

In addition, when the trehalose concentration in the trehalose solution can be set to 20 wt % to 35 wt %, tissue structure and strength in biological tissue before the treatment can be maintained to almost the same extent.

DESCRIPTION OF EMBODIMENTS

Example 1

First, a harvested bovine pericardium was made into the form of a 5-cm-by-7-cm rectangular sheet about 300 μm in thickness and 1.5 g in mass and washed with a phosphate buffered saline (PBS) containing an antibiotic.

Then, the washed bovine pericardium was subjected to acellularization by a method as already proposed by the present inventors (see Japanese Patent Laid-Open No. 2011-05043).

Next, 40 ml of a trehalose solution obtained by adding trehalose to PBS was provided, and the bovine pericardium after the acellularization (acellularized tissue) was placed together with the trehalose solution in a 50-ml centrifuge tube, the tube is shaken with the bovine pericardium impregnated with the trehalose solution. In this Example, the concentration of trehalose in the trehalose solution was set to 1 wt %. The shaking treatment was carried out at a revolution of 180 rpm for 24 hours using a bioshaker warmed at 37° C.

Thereafter, using a lyophilizer, the bovine pericardium was allowed to stand at about −45° C. for about 24 hours to remove the moisture of the bovine pericardium.

Then, in an ethylene oxide gas sterilizer, the bovine pericardium was sterilized with ethylene oxide gas to provide a sterilized dried tissue of the bovine pericardium. Here, the exposure temperature was set to 30° C.; the exposure time, to 12 hours; and aeration, to 20 hours.

Examples 2 to 9

A sterilized dried tissue of bovine pericardium was obtained as in Example 1 except that the concentration of trehalose in a solution thereof was changed. Specifically, the bovine pericardium acellularized as described above was placed in a trehalose solution whose trehalose concentration was set to each of 5, 10, 20, 25, 30, 35, 40, and 50 wt %, subjected to the above-described shaking treatment, and then dried and sterilized as described above to provide a sterilized dried tissue of the bovine pericardium according to each of Examples 2 to 9.

Also, the maximum concentration of trehalose was set to 50% because the concentration of trehalose dissolved in PBS at 37° C. was about 50%.

Examples 10 to 18

A sterilized dried tissue of bovine pericardium was obtained under the same conditions as in Examples 1 to 9 except that the acellularization was not conducted.

Examples 19 to 36

A sterilized dried tissue of bovine tendon was obtained under the same conditions as in Examples 1 to 18 except that a tissue to be treated was changed from bovine pericardium to bovine tendon.

Here, the bovine tendon used was in the order of 10 cm long and 10 mm thick.

Comparative Example 1

A sterilized dried tissue of bovine pericardium was obtained following a different procedure from that in Example 1, where the acellularized bovine pericardium was not impregnated with a trehalose solution, but dried and sterilized as described above.

Comparative Example 2

A sterilized dried tissue of bovine pericardium was obtained under the same conditions as in Comparative Example 1 without impregnation with a trehalose solution, except that the acellularization was not conducted.

Comparative Examples 3 and 4

A sterilized dried tissue of bovine tendon was obtained under the same conditions as in Comparative Examples 1 and 2 without impregnation with a trehalose solution, except that a tissue to be treated was changed from bovine pericardium to bovine tendon as in Example 19 and others.

Then, experiments for demonstrating the effect of the present invention were carried out.

As a first experiment, an experiment for demonstrating the effect of suppressing tissue degeneration according to the present invention was carried out using the sterilized dried tissue obtained in each of the above Examples and Comparative Examples.

Specifically, 40 ml of antibiotic-containing PBS is added to a 50-ml centrifuge tube, in which each sterilized dried tissue is placed. Then, it is shaken at a revolution of 180 rpm for 24 hours using a bioshaker warmed at 37° C., and the mass of the sterilized dried tissue thereby rehydrated was measured using an electronic balance. Then, the rate of increase in the mass of the sterilized dried tissue of each Example relative to that of the sterilized dried tissue of the corresponding Comparative Example without impregnation with a trehalose solution was calculated. The corresponding Comparative Example is Comparative Example 1 for Examples 1 to 9; the corresponding Comparative Example is Comparative Example 2 for Examples 10 to 18; the corresponding Comparative Example is Comparative Example 3 for Examples 19 to 27; and the corresponding Comparative Example is Comparative Example 4 for Examples 28 to 36.

As a second experiment, a tension test for demonstrating the effect of suppressing the strength reduction of tissue according to the present invention was carried out using the sterilized dried tissue obtained in each of the above Examples and Comparative Examples.

The experiment was carried out under the following conditions for each of Examples 1 to 18 and Comparative Examples 1 and 2 in which a bovine pericardium was used as a tissue to be treated.

After rehydrating each sterilized dried tissue of the bovine pericardium under the same conditions as those in the first experiment, a strip specimen of 3 mm wide was prepared, and a tension test was carried out by setting the initial chuck distance to 7 mm. The tension test was conducted under the conditions of an initial tension load of 0.5 N, a specimen elongation of 20%, a tensile speed of 120 mm/min, and a cycle number of 3,000. Then, for each specimen, the rate of stress relaxation over time was determined which was calculated by subtracting the load after 3,000 cycles from the initial load and dividing the balance by the initial load, and the rate of increase from the stress relaxation rate for the sterilized dried tissue of each of the corresponding Comparative Examples was calculated. The stress relaxation rate here is a measure of a viscoelastic characteristic (flexibility), and a larger stress relaxation rate means higher flexibility. The sterilization of biological tissue has been found to decrease the rate of stress relaxation compared to that before the treatment.

For each of Examples 19 to 36 and Comparative Examples 3 and 4 in which a bovine tendon was used as a tissue to be treated, the experiment was carried out under the following conditions.

Each specimen in the above-described shape was rehydrated under the same conditions as those in the first experiment, followed by performing a tension test by setting the width of the specimen to 4 mm and the initial chuck distance to 45 mm. The tension test was conducted under the conditions of an initial tension load of 66.7 N for 15 minutes and then the 10,000 cycles of a tension load of 100 N at a tensile speed of 300 mm/min. Then, for each specimen, the point was determined at which the percentage of increase in strain in every 100 cycles became less than 0.15%, and the influence of the crimp structure of collagen or the like constituting the tissue was eliminated as much as possible by subtracting a value of strain at the point where the percentage of increase in strain in every 100 cycles reached less than 0.15% from a value of strain until 10,000 cycles to calculate the rate of change in the strain of the tissue structure itself. The rate of change in strain here is similarly a measure of a viscoelastic characteristic. Then, for each specimen, the rate of increase in rate of change in strain relative to that of the sterilized dried tissue of corresponding Comparative Example was calculated.

The results of the experiments are shown in tables below.

TABLE 1

|  | Tissue | Acellularization | Trehalose Concentration (%) | Rate of Mass Increase (%) | Rate of Increase in Rate of Stress Relaxation (%) |
|---|---|---|---|---|---|
| Example 1 | Bovine Pericardium | YES | 1 | 5 | 11 |
| Example 2 | Bovine Pericardium | YES | 5 | 5 | 11 |
| Example 3 | Bovine Pericardium | YES | 10 | 5 | 21 |
| Example 4 | Bovine Pericardium | YES | 20 | 8 | 34 |
| Example 5 | Bovine Pericardium | YES | 25 | 13 | 52 |
| Example 6 | Bovine Pericardium | YES | 30 | 16 | 95 |
| Example 7 | Bovine Pericardium | YES | 35 | 12 | 34 |
| Example 8 | Bovine Pericardium | YES | 40 | 12 | 33 |
| Example 9 | Bovine Pericardium | YES | 50 | 9 | 30 |
| Comparative Example 1 | Bovine Pericardium | YES | 0 | 0 | 0 |

TABLE 2

|  | Tissue | Acellularization | Trehalose Concentration (%) | Rate of Mass Increase (%) | Rate of Increase in Rate of Stress Relaxation (%) |
|---|---|---|---|---|---|
| Example 10 | Bovine Pericardium | NO | 1 | 3 | 8 |
| Example 11 | Bovine Pericardium | NO | 5 | 5 | 16 |
| Example 12 | Bovine Pericardium | NO | 10 | 16 | 17 |
| Example 13 | Bovine Pericardium | NO | 20 | 21 | 23 |
| Example 14 | Bovine Pericardium | NO | 25 | 51 | 25 |
| Example 15 | Bovine Pericardium | NO | 30 | 57 | 60 |
| Example 16 | Bovine Pericardium | NO | 35 | 50 | 43 |
| Example 17 | Bovine Pericardium | NO | 40 | 27 | 37 |
| Example 18 | Bovine Pericardium | NO | 50 | 19 | 42 |
| Comparative Example 2 | Bovine Pericardium | NO | 0 | 0 | 0 |

TABLE 3

|  | Tissue | Acellularization | Trehalose Concentration (%) | Rate of Mass Increase (%) | Rate of Increase in Rate of Change in Strain (%) |
|---|---|---|---|---|---|
| Example 19 | Bovine Tendon | YES | 1 | 1 | 1 |
| Example 20 | Bovine Tendon | YES | 5 | 4 | 3 |
| Example 21 | Bovine Tendon | YES | 10 | 5 | 3 |
| Example 22 | Bovine Tendon | YES | 20 | 5 | 14 |
| Example 23 | Bovine Tendon | YES | 25 | 6 | 32 |
| Example 24 | Bovine Tendon | YES | 30 | 4 | 18 |
| Example 25 | Bovine Tendon | YES | 35 | 1 | 14 |
| Example 26 | Bovine Tendon | YES | 40 | 1 | 9 |
| Example 27 | Bovine Tendon | YES | 50 | 1 | 6 |
| Comparative Example 3 | Bovine Tendon | YES | 0 | 0 | 0 |

TABLE 4

|  | Tissue | Acellularization | Trehalose Concentration (%) | Rate of Mass Increase (%) | Rate of Increase in Rate of Change in Strain (%) |
|---|---|---|---|---|---|
| Example 28 | Bovine Tendon | NO | 1 | 9 | 11 |
| Example 29 | Bovine Tendon | NO | 5 | 14 | 7 |
| Example 30 | Bovine Tendon | NO | 10 | 17 | 9 |
| Example 31 | Bovine Tendon | NO | 20 | 18 | 52 |
| Example 32 | Bovine Tendon | NO | 25 | 18 | 54 |

TABLE 4-continued

|  | Tissue | Acellularization | Trehalose Concentration (%) | Rate of Mass Increase (%) | Rate of Increase in Rate of Change in Strain (%) |
|---|---|---|---|---|---|
| Example 33 | Bovine Tendon | NO | 30 | 18 | 57 |
| Example 34 | Bovine Tendon | NO | 35 | 15 | 23 |
| Example 35 | Bovine Tendon | NO | 40 | 10 | 18 |
| Example 36 | Bovine Tendon | NO | 50 | 5 | 10 |
| Comparative Example 4 | Bovine Tendon | NO | 0 | 0 | 0 |

The biological tissue treated by the conventional method (hereinafter referred to as "conventional treated tissue") has a decreased mass compared to that of the untreated tissue; however, according to the above experimental results, the biological tissue subjected to the treatment of the present invention (hereinafter referred to as "the treated tissue of the present invention") was enabled to have an increased mass compared to that of the conventional treated tissue. In addition, the trehalose concentration can be set to within the range of 20 wt % to 35 wt % to provide a peak of the highest mass among the treated tissues of the present invention, enabling the mass of the resultant tissue to be made at almost the same level as the mass of the untreated tissue. As a result, the present invention can be estimated to have the effect of suppressing the phenomenon of destroying the fine structure of tissue before treatment and was demonstrated to suppress the degeneration of biological tissue after treatment compared to the conventional method.

The conventional treated tissue has reduced strength compared to that of the untreated tissue due to reduced flexibility; however, according to the above experimental results, the treated tissue of the present invention was enabled to have increased flexibility and strength compared to those of the conventional treated tissue. In addition, the trehalose concentration can be set to within the range of 20 wt % to 35 wt % to provide a peak of the highest flexibility among the treated tissues of the present invention, enabling the flexibility thereof to be made at almost the same level as the flexibility of the untreated tissue. As a result, the present invention was demonstrated to suppress the strength reduction of biological tissue after treatment to a greater extent than the conventional method.

Further, according to the present invention, even when biological tissue was acellularized, tissue degeneration or strength reduction was demonstrated to be suppressed in the dried and sterilized tissue.

The present invention can be similarly applied, without being limited to the tissues of the above Examples, to any tissue provided that it is a tissue consisting of biological components and the like.

INDUSTRIAL APPLICABILITY

The present invention can be used for treatment for industrially processing or preserving a tissue harvested from an animal as a tissue for transplantation into a human body.

The invention claimed is:

1. A method for treating biological tissue, comprising:
a step of sterilizing biological tissue,
wherein the biological tissue is shaken in a state such that the biological tissue is impregnated with a trehalose solution before the sterilization step,
wherein the biological tissue is tendon, and
wherein the concentration of trehalose in the trehalose solution is 25 wt %.

2. A method for treating biological tissue, comprising:
a step of drying and then sterilizing biological tissue,
wherein the biological tissue is shaken in a state such that the biological tissue is impregnated with a trehalose solution before the drying step,
wherein the biological tissue is tendon, and
wherein the concentration of trehalose in the trehalose solution is 25 wt %.

3. A method for treating biological tissue, comprising:
a step of sterilizing acellularized biological tissue,
wherein the acellularized biological tissue is shaken in a state such that the biological tissue is impregnated with a trehalose solution before the sterilization step,
wherein the biological tissue is tendon, and
wherein the concentration of trehalose in the trehalose solution is 25 wt %.

4. Biological tissue obtained by shaking in a state such that the biological tissue is impregnated with a trehalose solution followed by drying and sterilization,
wherein the biological tissue is tendon, and
wherein the concentration of trehalose in the trehalose solution is 25 wt %.

5. Biological tissue obtained by shaking in a state such that the acellularized biological tissue is impregnated with a trehalose solution followed by drying and sterilization,
wherein the biological tissue is tendon, and
wherein the concentration of trehalose in the trehalose solution is 25 wt %.

6. The method according to claim 1, further comprising a step of washing the biological tissue with a phosphate buffered saline before shaking with the trehalose solution,
wherein the trehalose solution to be shaken with the biological tissue is a medium comprising the phosphate buffered saline and the trehalose.

7. The method according to claim 2, further comprising a step of washing the biological tissue with a phosphate buffered saline before shaking with the trehalose solution,
wherein the trehalose solution to be shaken with the biological tissue is a medium comprising the phosphate buffered saline and the trehalose.

8. The method according to claim 3, further comprising a step of washing the acellularized biological tissue with a phosphate buffered saline before shaking with the trehalose solution,
wherein the trehalose solution to be shaken with the biological tissue is a medium comprising the phosphate buffered saline and the trehalose.

9. The biological tissue according to claim 4,
wherein the biological tissue is obtained by steps further comprising a step of washing the biological tissue with a phosphate buffered saline before shaking with the trehalose solution, wherein the trehalose solution to be shaken with the biological tissue is a medium comprising the phosphate buffered saline and the trehalose.

10. The acellularized biological tissue according to claim 5,
wherein the acellularized biological tissue is obtained by steps further comprising a step of washing the acellularized biological tissue with a phosphate buffered saline before shaking with the trehalose solution, and
wherein the trehalose solution to be shaken with the biological tissue is a medium comprising the phosphate buffered saline and the trehalose.

\* \* \* \* \*